(12) United States Patent
Yamashita et al.

(10) Patent No.: US 8,525,984 B2
(45) Date of Patent: Sep. 3, 2013

(54) INSPECTION APPARATUS AND INSPECTION METHOD

(75) Inventors: Hiroyuki Yamashita, Hitachinaka (JP); Yukihisa Mohara, Hitachinaka (JP); Eiji Imai, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/469,071

(22) Filed: May 10, 2012

(65) Prior Publication Data

US 2012/0224173 A1 Sep. 6, 2012

Related U.S. Application Data

(60) Division of application No. 13/197,762, filed on Aug. 3, 2011, which is a continuation of application No. 12/771,842, filed on Apr. 30, 2010, now Pat. No. 7,999,932, which is a continuation of application No. 12/057,168, filed on Mar. 27, 2008, now Pat. No. 7,733,473.

(30) Foreign Application Priority Data

Mar. 28, 2007 (JP) .................................. 2007-083486

(51) Int. Cl.
*G01N 21/00* (2006.01)

(52) U.S. Cl.
USPC ..................................... 356/237.2; 356/237.5

(58) Field of Classification Search
USPC ..... 356/237.1–241.6, 242.1–243.8, 426–431, 356/600–640
See application file for complete search history.

(56) References Cited

U.S. PATENT DOCUMENTS

| | | | | |
|---|---|---|---|---|
| 4,233,625 A | * | 11/1980 | Altman | 348/87 |
| 4,557,599 A | * | 12/1985 | Zimring | 356/243.1 |
| 4,644,172 A | * | 2/1987 | Sandland et al. | 250/548 |
| 4,752,898 A | * | 6/1988 | Koenig | 356/400 |
| 4,985,676 A | | 1/1991 | Karasawa | |
| 5,163,012 A | * | 11/1992 | Wuhrl et al. | 382/112 |
| 5,617,182 A | | 4/1997 | Wakamoto et al. | |
| 5,905,850 A | * | 5/1999 | Kaveh | 700/259 |
| 5,936,420 A | * | 8/1999 | Sotokubo | 324/754.03 |

(Continued)

FOREIGN PATENT DOCUMENTS

| | | |
|---|---|---|
| JP | 2-54544 A | 2/1990 |
| JP | 4-093042 A | 3/1992 |

(Continued)

OTHER PUBLICATIONS

Office Action issued May 15, 2013, in Japanese Patent Application No. 2012-154724.

*Primary Examiner* — Gregory J Toatley
*Assistant Examiner* — Jarreas C Underwood
(74) *Attorney, Agent, or Firm* — Miles & Stockbridge P.C.

(57) ABSTRACT

An inspection apparatus includes a wafer stage for carrying a wafer, an illumination module which irradiates an inspection beam on the wafer carried on the wafer stage, a detection module which detects scattering rays or reflection rays from the wafer on the wafer stage and outputs an image signal, a coordinates control module which stores information about the arrangement of individual inspection areas on the wafer, and an imperfect area recognition module which recognizes, on the basis of the inspection area arrangement information stored in the coordinates control module, an imperfect inspection area interfering with a wafer edge.

10 Claims, 9 Drawing Sheets

(56) References Cited

U.S. PATENT DOCUMENTS

| | | | |
|---|---|---|---|
| 6,016,391 A * | 1/2000 | Facchini et al. | 716/55 |
| 6,118,515 A * | 9/2000 | Wakamoto et al. | 355/53 |
| 6,512,843 B1 | 1/2003 | Kuwabara | |
| 6,515,733 B1 * | 2/2003 | Udo | 355/53 |
| 6,781,688 B2 * | 8/2004 | Kren et al. | 356/237.4 |
| 6,980,917 B2 | 12/2005 | Ward et al. | |
| 7,243,325 B2 * | 7/2007 | McIntyre et al. | 716/55 |
| 7,324,917 B2 | 1/2008 | Koliopoulos et al. | |
| 7,657,077 B2 | 2/2010 | Michelsson et al. | |
| 7,733,473 B2 * | 6/2010 | Yamashita et al. | 356/237.2 |
| 7,738,693 B2 | 6/2010 | Luque | |
| 2004/0126004 A1 * | 7/2004 | Kikuchi | 382/141 |
| 2010/0053603 A1 | 3/2010 | Sakaguchi et al. | |

FOREIGN PATENT DOCUMENTS

| | | |
|---|---|---|
| JP | 06-036016 A | 2/1994 |
| JP | 7-209203 A | 8/1995 |
| JP | 7-321164 A | 12/1995 |
| JP | 10-173019 A | 6/1998 |
| JP | 2000-131240 A | 5/2000 |
| JP | 2001-236493 A | 8/2001 |
| JP | 2002-250699 | 9/2002 |
| JP | 2005-291833 A | 10/2005 |
| JP | 2006-252563 A | 9/2006 |
| JP | 2006-308372 A | 11/2006 |
| JP | 2007-67190 A | 3/2007 |

* cited by examiner

INSPECTION APPARATUS AND INSPECTION METHOD

CROSS-REFERENCE TO RELATED APPLICATION

This application is a division of U.S. application Ser. No. 13/197,762 filed Aug. 3, 2011, which is a continuation of application Ser. No. 12/771,842 filed Apr. 30, 2010 now U.S. Pat. No. 7,999,932, which is a continuation of application Ser. No. 12/057,168 filed Mar. 27, 2008 now U.S. Pat. No. 7,733,473.

BACKGROUND OF THE INVENTION

The present invention relates to inspection apparatus and inspection method for detecting foreign matters, flaws, contaminations and the like present on the surface of an object to be inspected such as a semiconductor wafer (hereinafter these defects will generally be described as foreign matters).

In an inspection apparatus for detecting foreign matters on a semiconductor wafer, an inspection optical beam such as a laser beam is irradiated on the surface of the wafer and reflection or scattering rays given off from the wafer surface are detected to detect a foreign matter present on the wafer surface.

In this type of inspection apparatus, when a pattern constituting chips is formed on the surface of the wafer, it is general practice that image signals are created from intensities of the detected reflection or scattering rays, an image signal of an inspection area (inspection chip or inspection shot) is compared with an image signal of a reference area (reference chip or reference shot) and a location where the difference between the two image signals exceeds a threshold value is determined as being indicative of a foreign matter (see JP-A-2002-250699). As the reference area, an area adjoining the inspection area (adjacent chip or adjacent shot) or an area of good quality prepared in advance (good quality chip or good quality shot) is used.

In inspecting the presence or absence of a foreign matter by comparing the inspection area with the reference area, an area having a perfect contour getting clear of a wafer edge (hereinafter referred to as a perfect area) is used as the reference area.

SUMMARY OF THE INVENTION

In the comparative inspection scheme as above, when inspecting an area having so imperfect a contour coming up to the wafer edge as to lack partly (hereinafter referred to as an imperfect area), an actually icon-existent portion outside the wafer edge gives rise to the difference in image signal with respect to the reference area irrespective of the presence or absence of any foreign matter. For this reason, the imperfect area is excluded from an inspection object precedently and cannot be inspected for the presence or absence of foreign matters.

With only the perfect area taken for an inspection area, however, the proportion of inspection areas on the wafer is lessened, leaving room for improvements in the accuracy of yield control.

The present invention has been made in the light of the above problems and it is an object of this invention to provide inspection apparatus and inspection method capable of improving the accuracy of yield control by inspecting an imperfect area efficiently.

To accomplish the above object, according to the present invention, an inspection apparatus comprises illumination means for irradiating an inspection optical beam on a wafer carried on a wafer stage, detection means for detecting scattering or reflected rays from the wafer and outputting an image signal, coordinates control means for storing information about the arrangement of individual inspection areas on the wafer, and imperfect area recognition means for recognizing an imperfect inspection area coming up to or interfering with a wafer edge on the basis of the inspection area arrangement information stored in the coordinates control means.

According to the present invention, the imperfect area coming up to the wafer edge can be inspected efficiently, attaining improvements in the accuracy of yield control.

Other objects, features and advantages of the invention will become apparent from the following description of the embodiments of the invention taken in conjunction with the accompanying drawings.

DESCRIPTION OF THE EMBODIMENT

The present invention will now be described by way of example with reference to the accompanying drawings.

Figure 1:
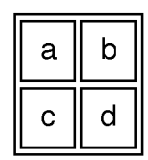
FIG. 1 is a diagram for explaining an inspection area.

Referring first to FIG. 1, an inspection area will be explained.

Firstly, a unit of exposure at a time is defined as a shot in the present specification. Assumptively, when exposure is effected in a unit of chip, a chip corresponds to a shot but a plurality of chips will sometimes be formed within one shot. In an example shown in FIG. 1, one shot is constituted by four chips a to d. In other words, the chips a to d are formed at a time through one exposure. As the case may be, the chips a to d are either of the same pattern or inclusive of a chip of different pattern. A shot in which a plurality of chips of different patterns exist is termed a multi-chip pattern. A reference area and an inspection area compared with it in a comparative inspection based on an inspection apparatus carrying out the present embodiment are each formed in the unit of chip or shot as above and a shot of multi-chip pattern will sometimes form a reference area or an inspection area.

Figure 2:
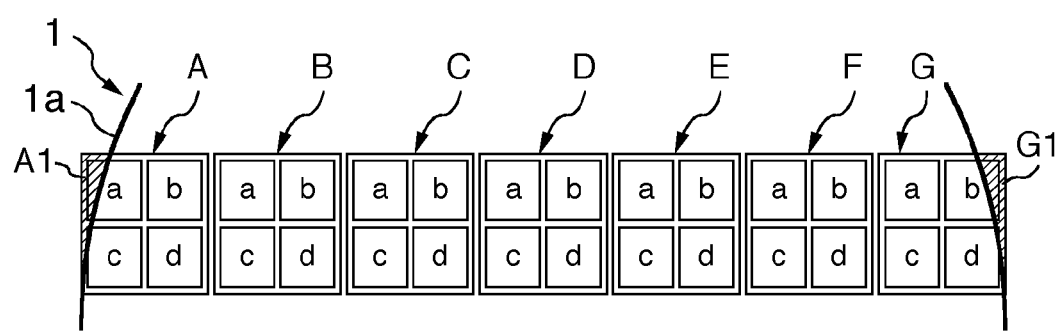
FIG. 2 is a diagram useful to explain perfect areas and imperfect areas.

Turning now to FIG. 2, a perfect area and an imperfect area will be explained.

Of shots A to G on wafer 1 as shown in FIG. 2, shots A and G coming up to a wafer edge 1a to have an imperfect contour in association with actually non-existent portions A1 and G1, respectively, are termed imperfect shots whereas shots B to F do not interfere with the wafer edge 1a to have perfect contours, being termed perfect shots. Then, taking the shot A, for instance, it includes chips a and c coming up to the wafer edge 1a to have an imperfect contour merging to the non-existent portion A1, so being termed imperfect chips, and chips b and d not interfering with the wafer edge 1a to have perfect contours, so being termed perfect chips. Each of the perfect shots B to F does not include any imperfect chip.

(1) Apparatus Construction

Figure 3:
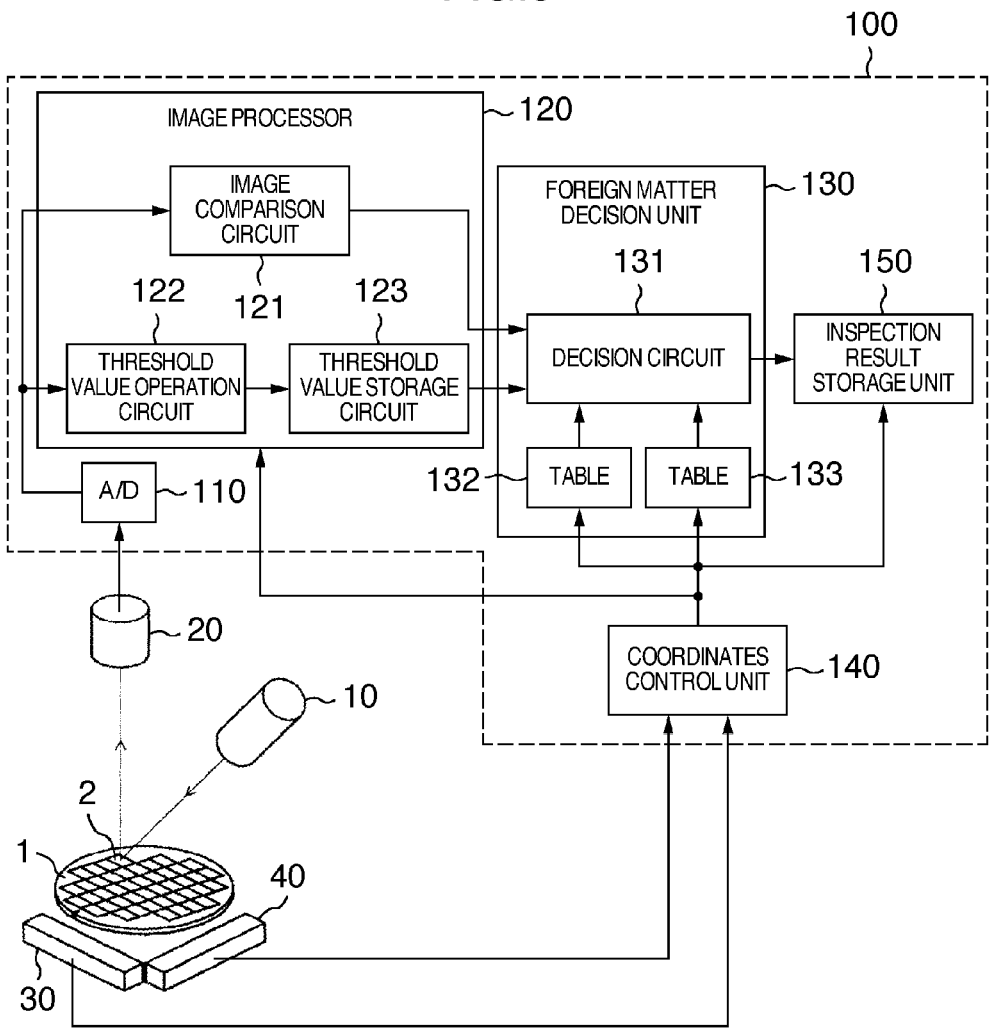
FIG. 3 is a block diagram schematically illustrating an inspection apparatus according to an embodiment of the invention.

Referring to FIG. 3, an inspection apparatus according to an embodiment of the invention is schematically illustrated therein.

The inspection apparatus as shown in FIG. 3 comprises an illumination unit 10, a detection unit 20, an X scale 30, a Y scale 40 and a processor 100. In the mode of the present embodiment, a description will be given by taking an instance where an optical inspection apparatus using a dark field image is applied to the inspection apparatus of this invention.

(1-1) Illumination Unit 10

The illumination unit 10 is a laser unit adapted to generate an inspection optical beam such as for example a laser beam of a predetermined wavelength and irradiate the inspection beam on the surface of a wafer 1 representing an object to be inspected. For example, the inspection beam may be irradiated obliquely to the surface of wafer 1. The wafer 1 having its surface formed with chips 2 is carried on a wafer stage (specimen stage) not shown. The wafer stage is carried on at least an XY stage so as to be movable in at least X and Y directions. As the wafer stage moves in the Y and X directions, the inspection beam emitted from the illumination unit 10 is scanned on the surface of wafer 1.

Figure 4:
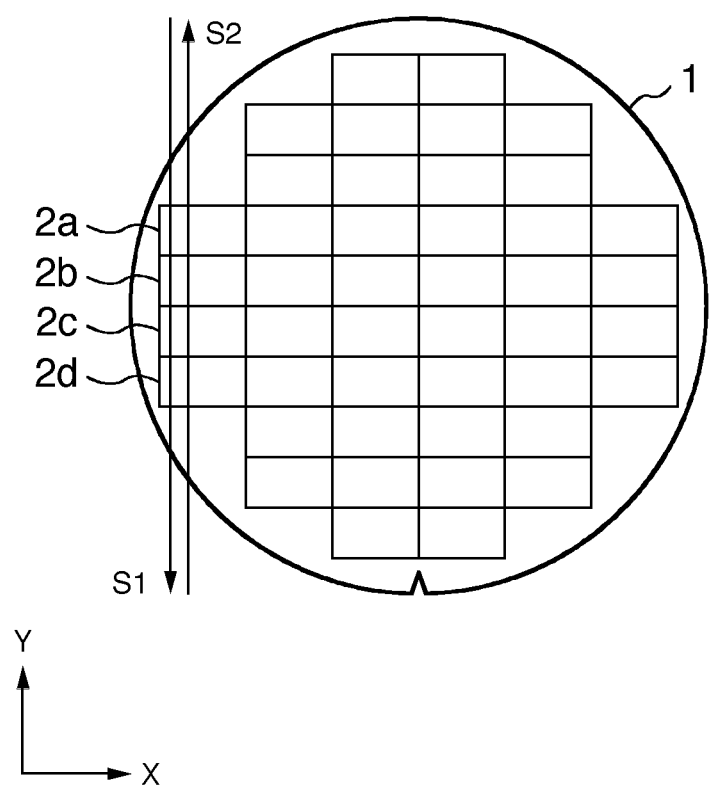
FIG. 4 is a diagram useful to explain the scanning of an inspection optical beam in the inspection apparatus according to the embodiment.

Scanning of the inspection beam in the inspection apparatus will be described with reference to FIG. 4.

As the wafer stage carrying the wafer 1 moves in the Y direction, the inspection beam emitted from the illumination unit 10 moves on surfaces of chips 2a, 2b, 2c and 2d formed on the wafer 1 in a direction indicated by arrow S1 to proceed with scanning of a first line. Subsequently, the wafer stage moves in the X direction to shift the scanning line in the X direction. Then, as the wafer stage moves in the Y direction in reverse to scanning of the first line, the inspection beam moves on the surfaces of chips 2d, 2c, 2b and 2a in a direction indicated by arrow S2, proceeding with scanning of a second line. By repeating these operations, the scanning on the overall surface of wafer 1 can be performed.

(1-2) Detection Unit 20

Reverting to FIG. 3, the inspection beam irradiated on the surface of wafer 1 is scattered by patterns and foreign matters on the surface of wafer 1, so that scattering rays are given off from the surface of wafer 1. For example, the detection unit 20 includes a focusing lens, a CCD and a TDI and operates to receive the scattering rays given off from the surface of wafer 1 and convert their intensities to electrical signals forming an image signal which in turn is delivered to the processor 100.

(1-3) X Scale 30 And Y Scale 40

The X scale 30 and Y scale 40 are laser scales, for example, and operate to detect X direction position and Y direction position of the wafer stage carrying the wafer 1 and deliver the positional information to the processor 100.

(1-4) Processor 100

The processor 100 includes an A/D converter 110, an image processing unit 120, a foreign matter decision unit 130, a coordinates control unit 140 and an inspection result storage unit 150.

(1-4. 1) A/D Converter 110

The A/D converter 110 converts the image signal in the form of an analog signal received from the detection unit 20 into an image signal in the form of a digital signal and delivers it.

(1-4. 2) Image Processing Unit 120

The image processing unit 120 includes an image comparison circuit 121, a threshold value operation circuit 122 and a threshold value storage circuit 123.

(1-4. 2. 1) Image Comparison Circuit 121

The image comparison circuit 121 has, for example, a delay circuit and a difference detection circuit and plays the role of a comparator for comparing an image signal of an inspection area detected by the detection unit 20 with an image signal, also detected by the detector unit 20, of corresponding pixels of a reference area and detecting a difference between the two image signals. The delay circuit receives the image signal from the A/D converter 110 and delays it to permit an image signal of an inspection area, which precedes by one an inspection area irradiated with the detection beam at present during scanning as shown in FIG. 4 and for which irradiation of the inspection beam has already been completed, to be delivered. The difference detection circuit receives from A/A converter 110 the image signal of the inspection area irradiated with the inspection beam at present and the image signal from the delay circuit as well to detect and deliver a difference between the two image signals. This ensures that the image comparison circuit 121 compares an image signal of the inspection area with an image signal of a reference area adjacent thereto. If a foreign matter exists on the surface of the inspection area, backscattering rays scattered by the foreign matter develop as a difference between the image signals of the mutually adjoining chips.

In addition to the aforementioned role of comparator, the image comparison circuit 121 fulfils, on the basis of information about the arrangement of inspection areas stored in the coordinates control unit 140, a role of an imperfect area recognition unit for recognizing an imperfect inspection area interfering with the wafer edge 1a and besides a role of a filter unit for excluding, from valid data, inspection data lying within the imperfect inspection area externally of the wafer edge 1a when the imperfect inspection area coming up to the wafer edge 1a is inspected.

It will be appreciated that the image comparison circuit 121 may substitute a memory adapted to store data of image signals of good-quality or acceptable chips prepared in advance for the delay circuit, thereby ensuring that comparison with an image signal of an acceptable inspection area can be performed.

(1-4. 2. 2) Threshold Value Operation Circuit 122

The threshold value operation circuit 122 functions as a threshold value operation unit which computes, on the basis of a statistical value (for example, a standard deviation) of image signals of mutually corresponding pixels of individual inspection areas, a threshold value for comparison with a difference from an image signal of the corresponding pixels of an inspection area. In other words, the threshold value operation circuit makes the correspondence of an image signal of an inspection area from the A/D converter 110 with an image signal of each reference area (inspection area now serving as reference area) from the delay circuit in respect of the individual pixels to compute a deviation (standard deviation) between individual inspection areas and calculates, on the basis of the deviation, threshold value data used for decision of the presence or absence of a foreign matter.

Further, during the threshold value calculation, the threshold value operation circuit 122 has the function to calculate a threshold value while excluding an image signal of pixels lying outside the wafer edge 1*a* on the basis of the information about the arrangement of inspection areas stored in the coordinates control unit 140. In this manner, the image signal of the pixels external of the wafer edge can be prevented from being used for calculation of the threshold value, ensuring the reliability thereof.

(1-4. 2. 3) Threshold Value Storage Circuit 123

In the threshold value storage circuit 123, threshold values inputted from the threshold value operation circuit 122 are saved by making the correspondence of these values with pieces of coordinate information of inspection areas inputted from the coordinates control unit 140.

(1-4. 3) Foreign Matter Decision Unit 130 The foreign matter decision unit 130 has a decision circuit 131 and coefficient tables 132 and 133.

(1-4. 3. 1) Coefficient Tables 132 And 133

In the coefficient tables 132 and 133, coefficients for changing the threshold values calculated by the threshold operation circuit 122 are stored while making the correspondence of the values with pieces of information about coordinates on the wafer. The coefficient tables 132 and 133 receive the coordinate information from the coordinates control unit 140 and deliver coefficients corresponding to the coordinate information to the decision circuit 131. Upon delivery to the decision circuit 131, the coefficients stored in the coefficient tables 132 and 133 are multiplied by threshold values at corresponding coordinates. Through this, when inspecting many identical products, for example, a flexible adjustment which depends on a portion inside the inspection area or a portion on the wafer (nearby the edge, for instance) liable to suffer from defects and the other portions can be made on the basis of cumulative old inspection/analysis data. In FIG. 3, the plural coefficient tables 132 and 133 are illustrated but a single coefficient table may suffice.

(1-4. 3. 2) Decision Circuit 131

Inputted to the decision circuit 131 are a difference signal between image signals of mutually corresponding pixels of the inspection area and the reference area which is delivered out of the image comparison circuit 121, threshold value data for the corresponding pixels read out of the threshold value storage circuit 123 and coefficients for changing threshold values for the corresponding pixels delivered out of the coefficient tables 132 and 133.

The decision circuit 131 creates threshold values for decision by multiplying the threshold value received from the image processor 120 by coefficients of corresponding pixels received from the coefficient tables 132 and 133. Then, the difference signal from the image comparison circuit 121 is compared with the decision threshold value for corresponding pixels to decide the presence or absence of foreign matters. In this example, when the difference signal exceeds the threshold, value for decision, the pixels in question are determined as being affected by scattering rays from foreign matters and the results of inspection are outputted to the inspection result storage unit 150. The decision circuit 131 also delivers the information of the threshold values used for decision to the inspection result storage unit 150.

In addition, the processor 100 (for example, decision circuit 131) may have the function to decide whether the inspection area is valid (of good quality) or invalid (of bad quality). In this case, an inspection area interfering with the wafer edge 1*a* externally thereof (inclusive of an inspection object representing an inspection area the whole of which is external of the wafer edge 1*a*) is invalid for a product, that is, from the product's viewpoint irrespective of the presence or absence of foreign matter and is therefore determined to be invalid. Next, when an inspection area is a chip inside a shot and if the chip per se does not interfere with the wafer edge 1*a*, being positioned inside the wafer edge 1*a* but the shot, to which the chip belongs, is an imperfect shot, the inspection area is determined to be an invalid inspection area so long as the difference (difference level) between an image signal (a statistical value such as mean value or cumulative value) of the whole inspection area (chip) and an image signal (a similar statistical value) of the whole reference area exceeds a set value.

Further, it is also conceivable to provide the function to decide the validity of each inspection area. What will be considered in this case is to gather statistics of the differences in signal intensities of individual pixels between the reference area and each inspection area and decide the validity of the inspection area on the basis of the statistical value. For example, the validity may be decided in terms of a percentage of the content of pixels for which the image signal difference from the reference area exceeds a set value or may be decided in accordance with the difference in image signal level (mean value or cumulative value) of the whole area of each inspection area from the reference area.

(1-4. 4) Coordinates Control Unit 140

On the basis of positional information of the wafer stage inputted from the X scale 30 and Y scale 40 (namely, positional information of wafer 1), the coordinates control unit 140 detects X and Y coordinates of a position on the wafer 1 at which the inspection beam is irradiated at present and delivers the detected coordinate information to the image processing unit 120, foreign matter decision unit 130 and inspection result storage unit 150. Also, the coordinates control unit 140 is stored with pieces of positional information about the arrangement of the individual inspection areas on the wafer 1. The arrangement information of individual inspection areas stored in the coordinates control unit 140 is outputted to the image processing unit 120 and coefficient tables 132 and 133 as described previously.

(1-4. 5) Inspection Result Storage Unit 150

The inspection result storage unit 150 stores the results of inspection received from the foreign matter decision unit 130 and the coordinate information of corresponding pixels received from the coordinates control unit 140 by making the correspondence of the inspection results with the coordinate information pieces. The inspection result storage unit 150 also stores the information indicative of threshold values received from the foreign matter decision unit 130 by making the correspondence of this information with the inspection results or coordinate information pieces of the corresponding pixels.

(2) Inspection Procedures

Procedures of inspection of an imperfect inspection area (imperfect chip or imperfect shot) by means of the processor 100 of inspection apparatus constructed as above will be described.

Figure 5:
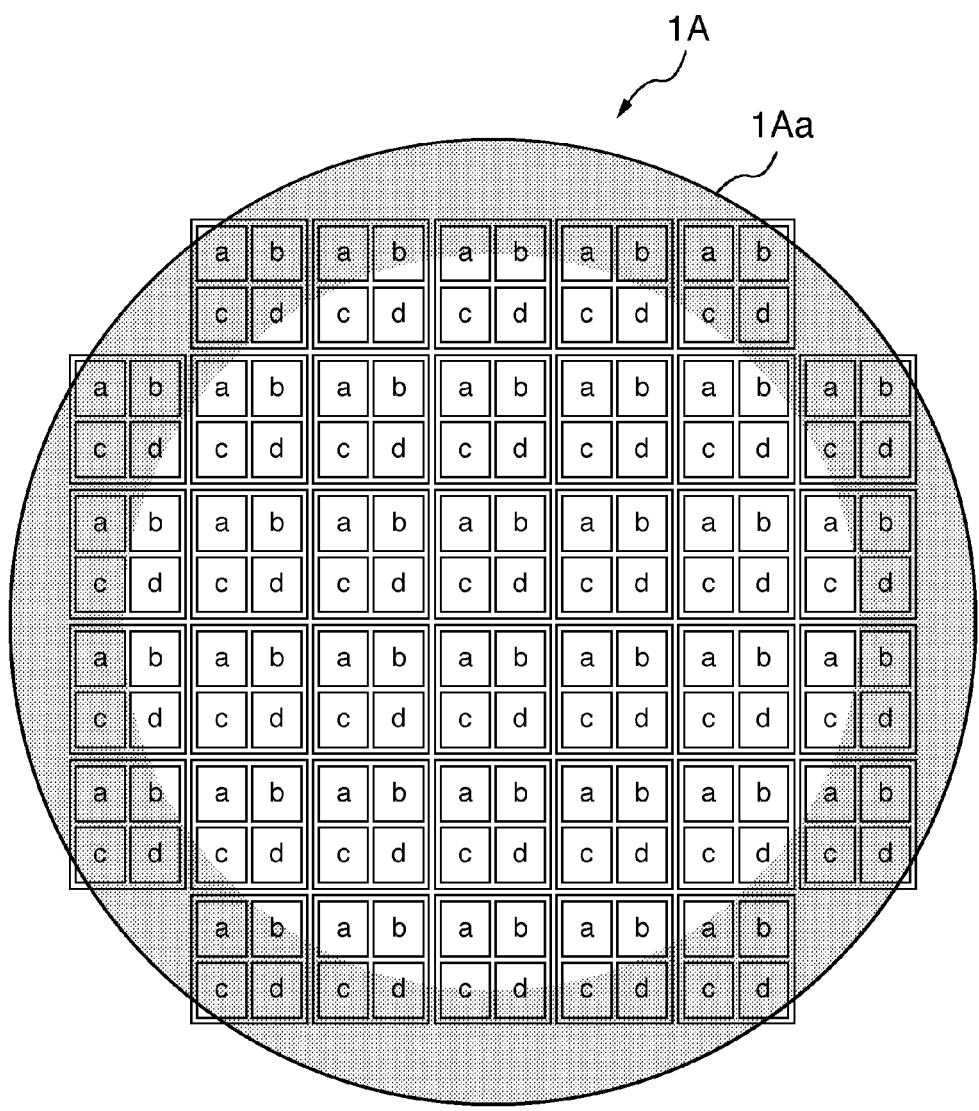
FIG. 5 is a diagram schematically illustrating the whole of a wafer representing an inspection specimen.

The whole of a wafer 1A representing an inspection specimen is schematically illustrated in FIG. 5.

The wafer 1A shown in FIG. 5 is a multi-chip pattern having four different chips a to d arranged similarly in each shot. A shot arranged at a left upper edge of wafer 1A is an imperfect shot having an imperfect chip (chip a) at its left upper portion. Likewise, shots arranged at left lower, right upper and right lower edges are imperfect shots including imperfect chips (chips b, c and d) at their right upper, left lower and right lower portions, respectively. According to the mode of the present embodiment, in inspecting a chip inside an imperfect shot (for example, chip a), a comparative inspection is carried out by using as a reference area a corresponding chip (chip a) of a perfect shot adjoining the imperfect shot in the scanning direction of the inspection beam on the side close to the center line of wafer 1A (center line orthogonal to scanning direction).

When inspecting foreign matters on the wafer 1A, the processor 100 first receives information about the arrangement of inspection areas on the wafer 1A from the coordinates control unit 140 by way of the image processing unit 120 and on the basis of the inputted inspection area arrangement information, recognizes an imperfect inspection area interfering with a wafer edge 1Aa. The image processing unit 120 sets information about the imperfect inspection area (for example, information of coordinates of a non-existent portion) to the image comparison circuit 121 and threshold value operation circuit 122.

Subsequently, an inspection beam is irradiated on the wafer 1A by means of the illumination unit 10 and while scanning the inspection beam by moving the wafer stage not shown, scattering rays from the wafer 1A are detected with the detection unit 20 and an image signal created by the detection unit 20 is delivered to the image processing unit 120.

Thereafter, in synchronism with the positional information of wafer stage (coordinate information of a beam spot) inputted from the coordinates control unit 140, the threshold value operation circuit 122 calculates threshold values used for decision of foreign matters in respect of individual pixels in an inspection area on the basis of the image information of the inspection area inputted through the A/D converter 110. In this phase, the threshold value operation circuit 122 excludes an image signal of a non-existent portion associated with an imperfect inspection area from the threshold value operation on the basis of information about the imperfect inspection area inputted from the coordinates control unit 140 and calculates a threshold value for individual pixels by making statistics of valid image signals of corresponding pixels in each inspection area. The threshold values for individual pixels calculated by the threshold value operation circuit 122 are stored in the threshold value storage circuit 123 by making the correspondence of them with the pieces of coordinate information.

Concurrently with (or before or after) the threshold value calculation by the threshold value operation circuit 122, the image comparison circuit 121 compares, in synchronism with the positional information of wafer stage (coordinate information of the beam spot) inputted from the coordinates control unit 140, the image information of inspection area inputted through the A/D converter 110 with the image information of a reference area inputted from the delay circuit to calculate the difference in intensities of the individual pixels between the two image signals and delivers the results of calculation to the foreign matter decision unit 130. In connection with at least an imperfect inspection area for which the existence of a non-existent portion has been recognized in advance, the comparison is made with a reference area contiguous in the scanning direction on the side close to the wafer centerline. In this phase, on the basis of the information of the imperfect inspection area inputted from the coordinate control unit 140, the image comparison circuit 121 excludes from valid data the result of the comparison of the non-existent portion of imperfect inspection area with the reference area.

Next, the presence or absence of foreign matter is decided with the foreign matter decision unit 130. The decision circuit 131 of foreign matter decision unit 130 compares a signal from the image comparison circuit 121 indicative of the difference between image signals of corresponding pixels of inspection area and reference area with a threshold value for decision and decides the presence or absence of a foreign matter in accordance with the magnitude relative to the decision threshold value. As the decision threshold value in this case, the value outputted from the image processing unit 120 may be used as it is but in order to reflect tendency toward detection of foreign matters on the basis of the past detection result and analysis result and depending on portions of a product in accordance with coordinates of the inspection areas and so to further improve the yield, a value may be computed by multiplying threshold data for corresponding pixels read out of the threshold value storage circuit 123 by coefficients adjusted in compliance with the portion (corresponding coordinates) of the product inputted from the coefficient tables 132 and 133.

The thus obtained results of foreign matter decision are outputted to the inspection result storage unit 150 which in turn stores the foreign matter decision results by making the correspondence of them with the coordinate information. The information about the foreign matter inspection results stored in the inspection result storage unit 150 can be transferred to an information processor (such as PC) external of the inspection apparatus and used as yield information.

In parallel with the above foreign matter inspection, the processor 100 decides the validity of each inspection area for a product or from the product's viewpoint.

Figure 6:
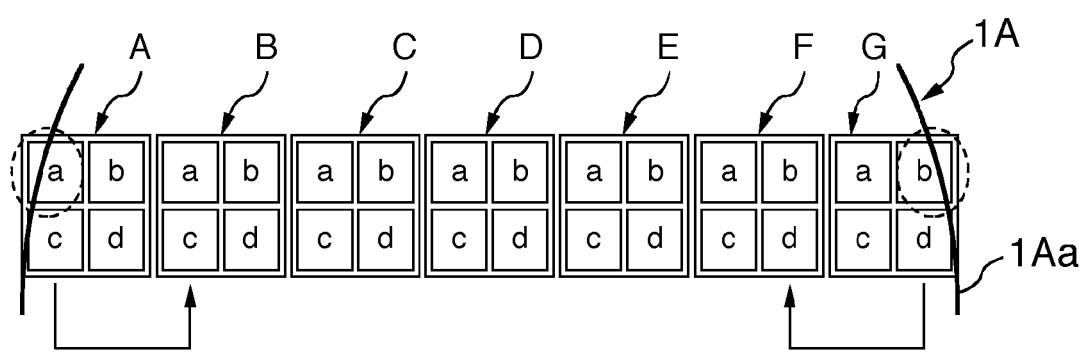
FIG. 6 is a diagram for explaining procedures of inspecting foreign matters at imperfect inspection areas.

For example, the decision circuit 131 first determines invalidity (defectiveness) of an inspection area interfering with the wafer edge 1Aa such as for example chip a or b contoured by circle in shot A or G in FIG. 6 (including an inspection area the whole of which is outside the wafer edge 1Aa when it is an object to be inspected).

Next, in the case of the inspection area being a chip, when the chip per se does not interfere with the wafer edge 1Aa to lie internally thereof but a shot including the chip is an imperfect shot, the difference between an image signal (statistical value such as mean value or cumulative value) of the whole of inspection areas (chips) and an image signal (similarly, statistical value) of the whole of reference areas is compared with the set value and a chip for which the difference exceeds the set value is determined as invalid (defective). In this case, the inspection chip is compared with a corresponding chip (reference chip) of an internally adjoining shot as shown at arrow in FIG. 6.

Statistics of the difference in intensity of an image signal of individual pixels of the reference area described as above are made not only for the imperfect chip or the perfect chip included in the imperfect shot but also for the remaining inspection areas (in other words, all of the inspection areas) and on the basis of the statistical values, the validity of the inspection area can be decided.

The decision result of the validity of inspection area from the product's viewpoint is also outputted to the inspection result storage unit 150, which in turn stores the decision result by making the correspondence of it with the coordinate information. The information about validity stored in the inspection result storage unit 150 can also be transferred to the information processor (such as PC) external of the inspection apparatus and used as yield information.

(3) Operation And Effects

As described above, according to the present embodiment, not only a perfect area lying internally of a wafer edge and having a perfect contour but also an imperfect area interfering with the wafer edge can be inspected validly. Accordingly, by acquiring a sufficient amount of information by increasing the proportion of inspection areas on the wafer, the accuracy of yield control can be improved.

Figure 7A:
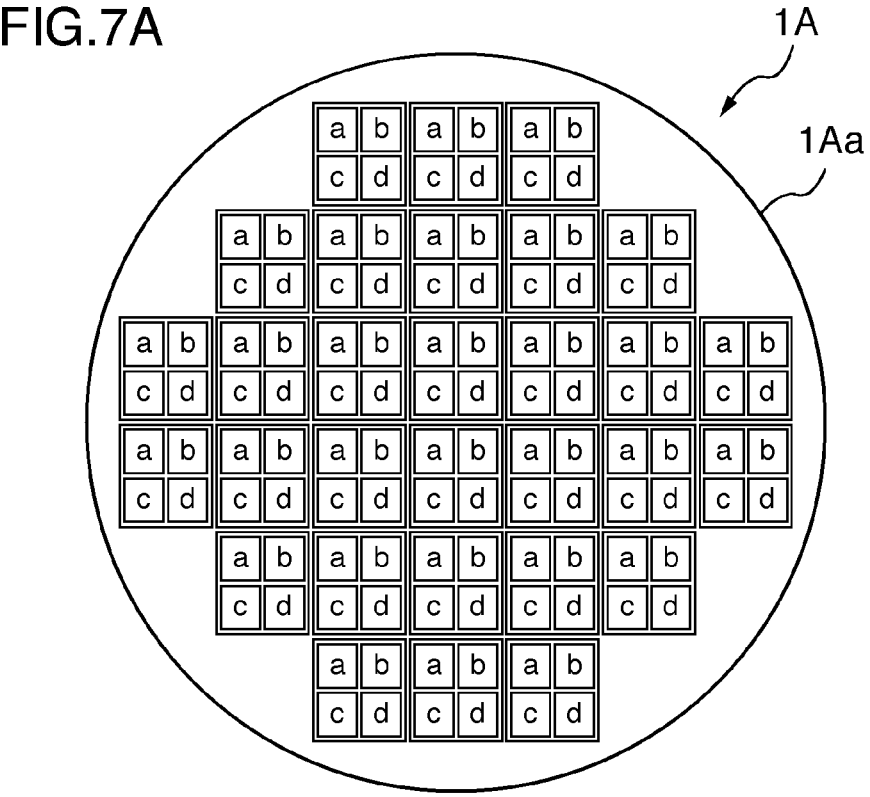
FIGS. 7A and 7B are diagrams illustrative of the difference in area to be inspected between a case (comparative example) unapplied with the invention and a case applied with the invention.
Figure 7B:
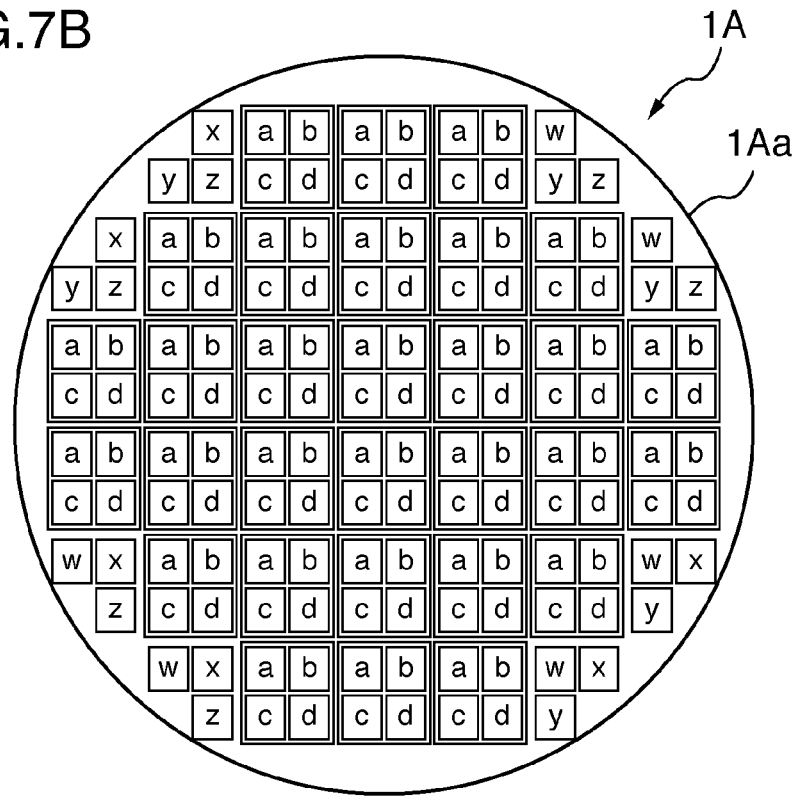

Referring to FIGS. 7A and 7B, the difference in area representing an object to be inspected between the case where the present embodiment is not applied to the wafer of FIG. 5 (comparative example) and the case where the present embodiment is applied.

If the present embodiment is not applied especially in the case of a multi-chip pattern, the quality can be decided in only a unit of shot and a shot including an imperfect chip is excluded from the inspection object regardless of whether a perfect chip is included or not. Consequently, in the comparative example as shown in FIG. 7A, not only the imperfect chip but also the shot inclusive of it is excluded from the inspection object and perfect chips included in the imperfect shot fail to be determined as valid chips.

Contrary to this, in the present embodiment, a perfect chip having a perfect contour by itself can be an object of validity inspection even when a shot to which the perfect chip belongs is imperfect and therefore, perfect chips w, x, y and z included in individual imperfect shots are added to the inspection object as shown in FIG. 7B, thereby increasing the amount of yield information as compared to the comparative example in FIG. 7A.

The ability to decide the degree of valid chip can also contribute to an increase in the amount of acquired information and yet an improvement in the accuracy of yield control.

Figure 8:
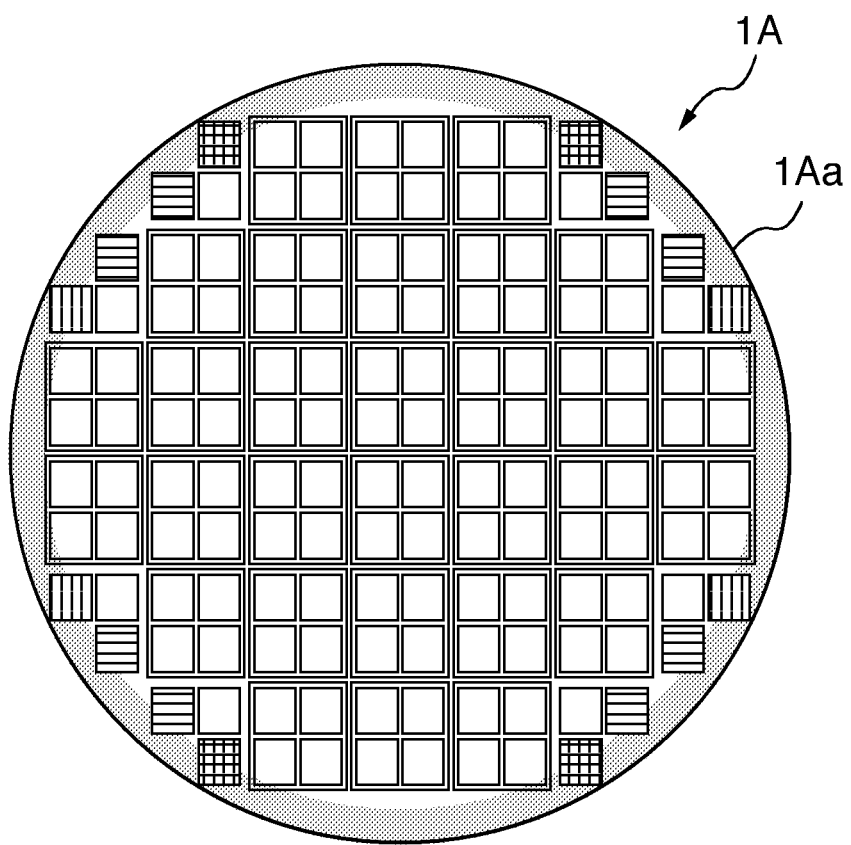
FIG. 8 is a diagram depicting an example capable of displaying the degree of validity of chips on the operation screen in a visually recognizable fashion.

Illustrated in FIG. 8 is an example where the valid chip degree is displayed visually recognizably on, for example, the operation screen.

In FIG. 8, degrees of the chip validity are distinguished in different hatching patterns but they may be displayed distinguishably in different colors. In the display example of FIG. 8, the majority of areas each presumed to have a sufficiently high validity degree are so set as to be devoid of hatching display in order to avoid complexity. Further, for an inspection area fully interfering with the wafer edge 1Aa and being necessarily invalid, display is so set as to be omitted.

Figure 9:
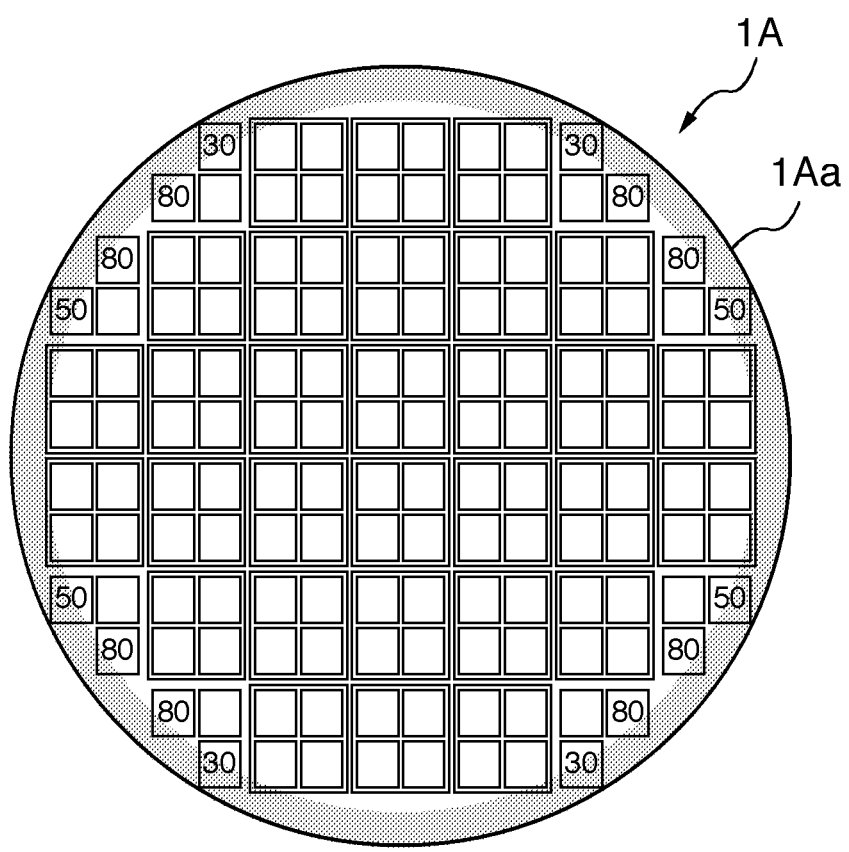
FIG. 9 is a diagram depicting an example displaying the validity degree in numerical values.

Illustrated in FIG. 9 is an example of displaying the valid chip degree in numerical values.

In FIG. 9, the validity degree of each inspection area is displayed in numerical value. In this display example, the majority of areas each presumed to have a sufficiently high validity degree (area of validity degree 100) are so set as to be devoid of numerical value display in order to avoid complexity. Further, for an inspection area fully interfering with the wafer edge 1Aa and being necessarily invalid (necessarily an area of validity degree 0), display is so set as to be omitted.

Figure 10:
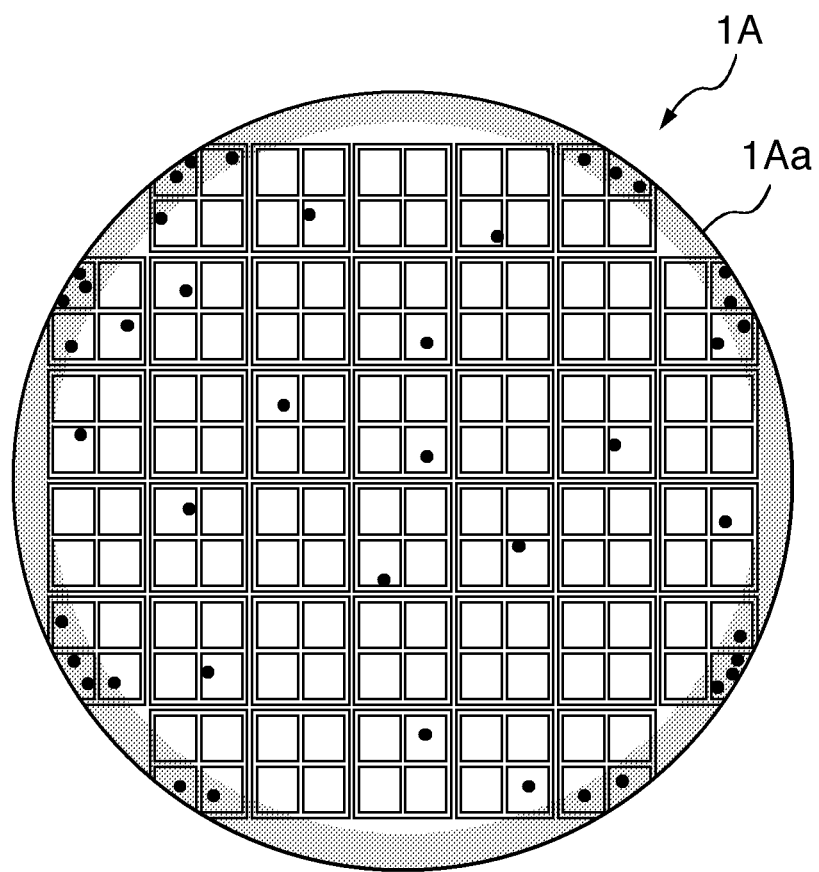
FIG. 10 is a diagram illustrating an example of displaying the result of inspection of all foreign matters on inspection permissible areas inclusive of imperfect chips.

Further, in the mode of the present embodiment, even an imperfect chip can be compared with a corresponding chip of an internally adjoining shot during foreign matter inspection and hence, for areas of the imperfect chip which are internal of the wafer edge 1Aa, the foreign matter inspection can be executed validly. Therefore, as shown in FIG. 10, the results of inspection of all foreign matters on areas capable of being inspected inclusive of invalid chips can be acquired. In FIG. 10, detected foreign matters in dot shape are displayed in association with the arrangement of chips on the wafer 1A. In this manner, information about foreign matter at areas near the wafer edge 1Aa, which areas are prone to exfoliation due to uneven film and unstable quality, can be acquired efficiently, contributing to improvements in the accuracy of yield.

(5) Miscellany

As described previously, the inspection according to the present embodiment can be applied not only to the wafer of multi-chip pattern but also to a wafer having a plurality of identical chips which are exposed simultaneously through one shot and besides can be applied to an inspection in a unit of shot and an inspection in a unit of chip as well.

In the inspection apparatus to which the present invention is applied, the direction of irradiation of the inspection beam on the wafer 1 is not particularly limited but the present invention is applicable to both an inspection apparatus in which the inspection beam is irradiated obliquely to the wafer 1 and an inspection apparatus in which the inspection beam is irradiated vertically.

The present invention has been described as being applied to the inspection apparatus using a dark field image attributable to scattering rays generated on the surface of a wafer under irradiation of the inspection beam on the wafer surface but this is not limitative and the invention can also be applied to an inspection apparatus using a bright field image attributable to reflection rays from the wafer surface, attaining advantageous effects similarly.

Further, the foregoing embodiment has been described by way of example of the inspection apparatus in which both the foreign matter inspection and the decision of validity degree of each inspection area can be practicable but when utilization is limited to one of them, one of the functions of foreign matter inspection and inspection area validity degree decision may be omitted.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus for inspecting a substrate, the inspection apparatus comprising:
    an illumination unit which illuminates the substrate with light, the substrate including a first area having only part of a first pattern thereon and a second area having at least part of a second pattern thereon, the first and second areas constituting portions of a third area, wherein the first area is missing a portion corresponding to another part of the first pattern such that the first pattern is only partially formed on the substrate;
    a detection unit which detects light from the illuminated substrate and generates a signal of an image based on the detected light, the image including the first and second areas;
    a memory which stores arrangement information of the first, second and third areas; and
    a processing unit which uses the arrangement information to recognize imperfection of at least one of the first and second areas.

2. The inspection apparatus according to claim 1, further comprising:
    a scanning unit which performs a scanning motion relatively between the substrate and the illumination unit so as to scan the substrate using the illumination unit, wherein
    the processing unit uses signals of an image including the imperfection and a reference image to determine existence of a defect, and wherein
    the reference image is an image of an area which, relative to the area including the imperfection, is located on a side close to a center line of the substrate orthogonal to a scanning direction of the scanning unit.

3. The inspection apparatus according to claim 2, wherein the reference image is an image of a perfect area having no defect.

4. The inspection apparatus according to claim 1, wherein the processing unit acquires a threshold value for inspection by using signals of the image except for an imperfect portion thereof associated with the imperfection.

5. The inspection apparatus according to claim 1, wherein the processing unit compares an image of a perfect area with a reference image.

6. An inspection method comprising:
    illuminating a substrate with light, the substrate including a first area having only part of a first pattern thereon and a second area having at least part of a second pattern thereon, the first and second areas constituting portions of a third area, wherein the first area is missing a portion corresponding to another part of the first pattern such that the first pattern is only partially formed on the substrate;
    detecting light from the illuminated substrate and generating a signal of an image based on the detected light, the image including the first and second areas;
    recognizing, by use of arrangement information of the first, second and third areas stored in a memory, imperfection of at least one of the first and second areas.

7. The inspection method according to claim 6, further comprising:
    performing a scanning motion relatively between the substrate and the illumination light, and
    using signals of an image including the imperfection and a reference image to determine existence of a defect,
    wherein the reference image is an image of an area which, relative to the area including the imperfection, is located on a side close to a center line of the substrate orthogonal to a scanning direction of the scanning motion.

8. The inspection method according to claim 7, wherein the reference image is an image of a perfect area having no defect.

9. The inspection method according to claim 6, which includes acquiring a threshold value for inspection by using signals of the image except for an imperfect portion thereof associated with the imperfection.

10. The inspection method according to claim 6, which includes comparing an image of a perfect area with a reference image.

* * * * *